United States Patent [19]
Vicenzi

[11] Patent Number: 5,281,225
[45] Date of Patent: Jan. 25, 1994

[54] INTRAMEDULLARY PIN WITH SELF-LOCKING END FOR METADIAPHYSEAL FRACTURES OF LONG BONES

[76] Inventor: Guglielmo Vicenzi, Via Carducci 11, 41034 Finale Emilia, Italy

[21] Appl. No.: 525,826

[22] Filed: May 21, 1990

[30] Foreign Application Priority Data

Jun. 7, 1989 [IT] Italy ............................ 3508 A/89
Apr. 30, 1990 [IT] Italy ............................ 3468 A/90

[51] Int. Cl.$^5$ ............................................. A61B 17/56
[52] U.S. Cl. ........................................ 606/62; 606/63; 606/64
[58] Field of Search ............... 606/64, 67, 72, 80, 606/84, 86, 96, 104, 65, 66, 73

[56] References Cited

U.S. PATENT DOCUMENTS

| | | | |
|---|---|---|---|
| 3,441,017 | 4/1969 | Kaessmann | 606/64 |
| 4,011,863 | 3/1977 | Zickel | 606/62 |
| 4,135,507 | 1/1979 | Harris | 606/64 |
| 4,653,481 | 3/1987 | Howland | 606/61 |
| 4,773,402 | 9/1988 | Asher | 606/61 |
| 4,852,559 | 8/1989 | Chernoff | 606/62 |
| 4,915,092 | 4/1990 | Firica | 606/64 |
| 5,013,314 | 5/1991 | Firica | 606/104 |
| 5,034,012 | 7/1991 | Frigg | 606/62 |
| 5,108,397 | 4/1992 | White | 606/60 |

FOREIGN PATENT DOCUMENTS

| | | | |
|---|---|---|---|
| 0923085 | 7/1949 | Fed. Rep. of Germany | 30/903 |
| 3146065 | 5/1983 | Fed. Rep. of Germany | A61B 17/18 |
| 1146824 | 11/1957 | France | 606/62 |
| 2512340 | 3/1983 | France | A61B 17/18 |
| 9004948 | 5/1990 | World Int. Prop. O. | 606/61 |

Primary Examiner—Michael A. Brown
Attorney, Agent, or Firm—Guido Modiano; Albert Josif

[57] ABSTRACT

Intramedullary pin with self-locking end for metadiaphyseal fractures, constituted by a proximal stub provided with means for fixing to the cortices; the ends of at least two curved and elastically deformable stems are axially rigidly associated with the stub, and the stems are adapted to expand elastically and to press with their tips the walls of the bone from the inside of the medullary canal.

17 Claims, 2 Drawing Sheets

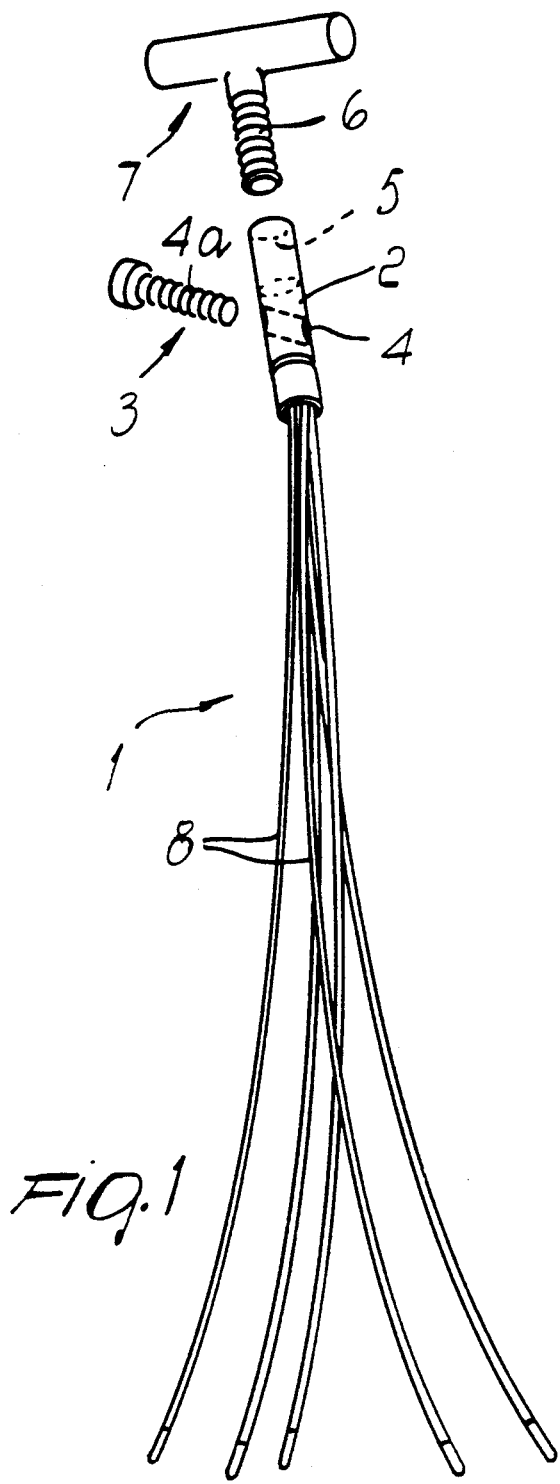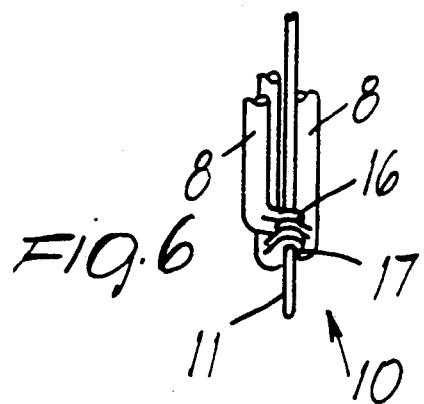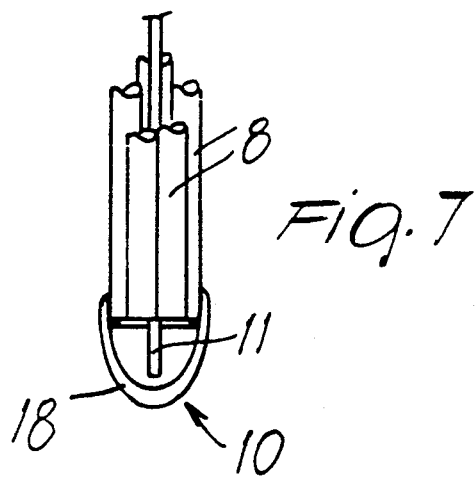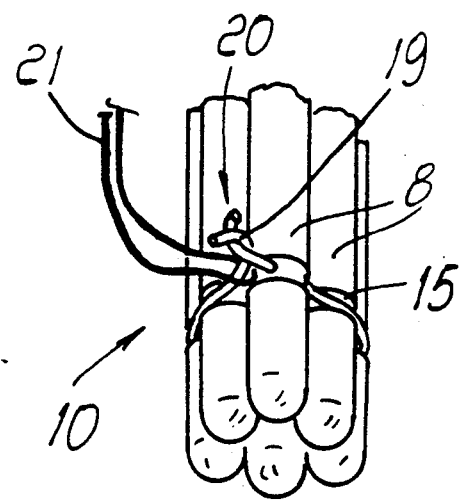

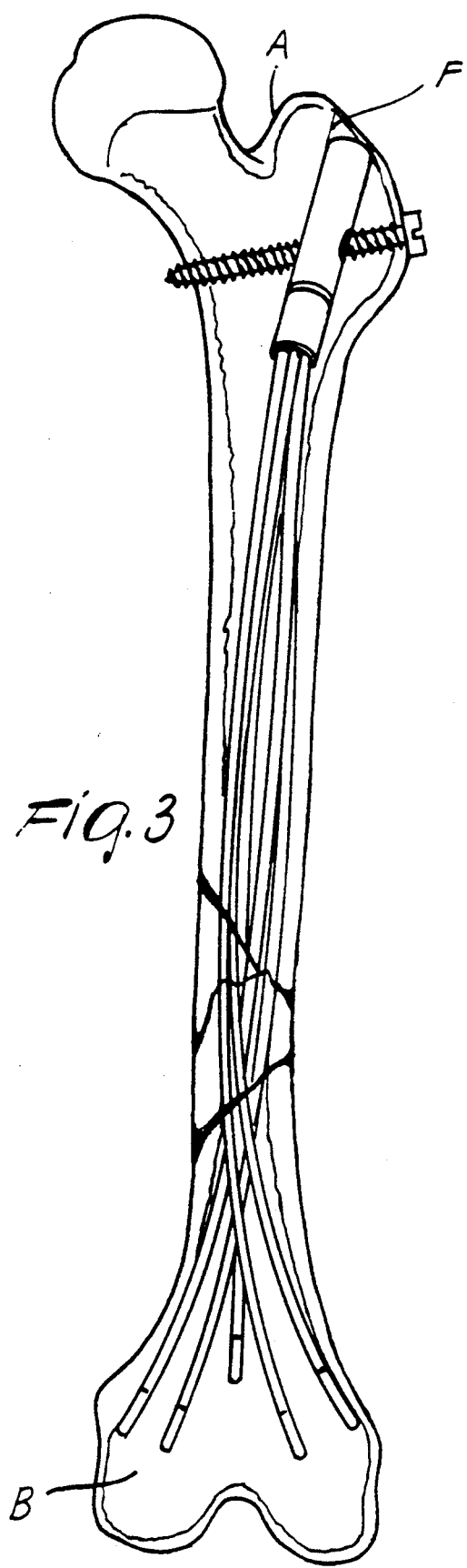
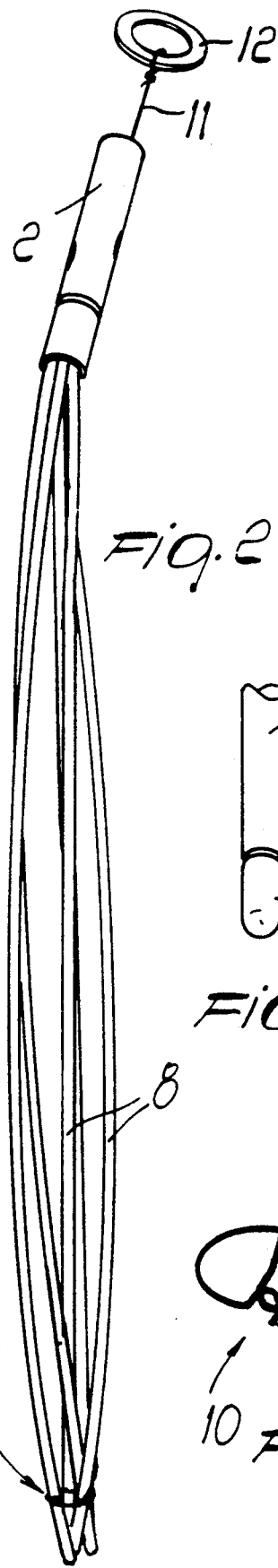
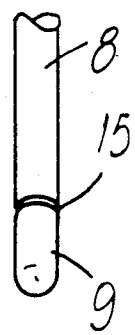
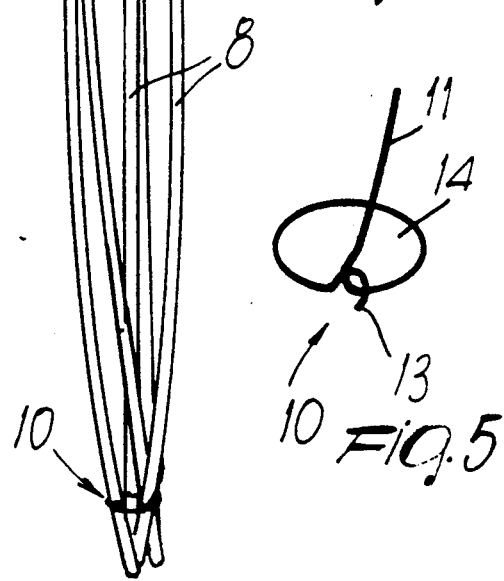

INTRAMEDULLARY PIN WITH SELF-LOCKING END FOR METADIAPHYSEAL FRACTURES OF LONG BONES

BACKGROUND OF THE INVENTION

The present invention relates to an intramedullary pin for metadiaphyseal fractures of long bones.

It is known to intervene with intramedullary pins or the like to reduce metadiaphyseal fractures, i.e. fractures involving the intermediate part of long bones; the ends of said pins can or must be fixed with screws to both the intact cortices of the bone (i.e. the proximal cortex and the distal cortex), and fixing by means of screws to both of the cortices entails some disadvantages due, among other things, to the fact that additional surgical time is required and that it is often necessary to resort to radiological means for rather long times in order to determine the fixing position of the screws in the pin, with consequent exposure to the surgeon, to the assistants and to the operating-theater personnel of ionizing radiation even for prolonged periods of time.

Besides this, when the pin is to be removed at the end of the treatment, it is necessary to intervene not only in the region of the bone from which the pin is to be extracted but also distally, where the fixing screws must be removed.

SUMMARY OF THE INVENTION

The technical aim of the present invention is to obviate the above disadvantages of known intramedullary pins, i.e. to provide a pin which does not require interventions from outside for distal pin-bone coupling, which allows an elastic osteosynthesis, which can be locked at one end with a screw (when desired or required) and rapidly self-locks at the other end, which can be installed very quickly requiring only an extremely short exposure to radiation, which does not require drilling nor preliminary preparation of the medullary canal and which can be even more easily removed when the fracture has been repaired.

Within the scope of this technical aim, an object of the present invention is to provide a pin which can be installed with a set of instruments which is extremely simple, is inexpensive and adapts to various dimensional situations of the bone in which it is installed, so that a very small number of sizes is sufficient to satisfy any requirement.

Another object of the present invention is to solve the above aim and object by means of a simple structure which is relatively easy to execute in practice, safe in use and effective in operation as well as relatively modest in cost.

This aim and these objects are achieved by the present intramedullary pin with self-locking end for metadiaphyseal fractures of long bones, characterized in that it is constituted by a proximal stub which is provided with means for fixing to the proximal cortices, the ends of at least two curved and elastically deformable stems being axially rigidly associated with said stub, said stems having temporary retention means at their free ends, said means being adapted to keep the tips of the stems mutually adjacent during the insertion of the pin in the medullary canal through the metadiaphysis and to release the tips when the pin is in correct position so as to allow the elastic widening of the stems, the tips whereof anchor in the intramedullary spongy bone until they possibly press the inner walls of the bone, producing an integral coupling between the synthesis means and the bone.

BRIEF DESCRIPTION OF THE DRAWINGS

Further particularities will become apparent and evident from the detailed description of a preferred but not exclusive embodiment of an intramedullary pin according to the invention, illustrated only by way of non-limitative example in the accompanying drawings, wherein:

FIG. 1 is a perspective side view of an open pin according to the invention;

FIG. 2 is a side view of the closed pin of FIG. 1 before it is inserted in the bone;

FIG. 3 is a schematic and sectional view of a pin inserted in the bone.

FIGS. 4 to 8 are views of provided retaining means of the stems.

DESCRIPTION OF THE PREFERRED EMBODIMENTS

With particular reference to the above figures, the reference numeral 1 indicates the intramedullary pin according to the invention for metadiaphyseal fractures of long bones, i.e. fractures which leave the ends practically intact.

The pin 1 is constituted by a proximal stub 2 which is provided with means 3 for fixing to the cortices; said means are advantageously constituted by a screw 4a the stem whereof can be screwed into an oblique hole 4 of the stub which can be threaded or not; at one end, the stub has an axial threaded hole 5 in which the stem 6 of a T-shaped grip handle 7, which facilitates the operations of inserting and extracting the pin, can be screwed.

At the other end, the stub has at least two (five in the particular illustrated case) elastically deformable curved stems 8 (advantageously made of biocompatible steel such as for example AISI 316L) rigidly associated therewith; said stems can have a circular cross section and rounded ends 9; advantageously, one of the stems, for example the central one, is slightly longer than the others so as to define, when the stems are gathered in a bundle, a pointed assembly free end 1a which is easier to orientate and insert in bone cavities.

In order to improve load distribution and avoid fractures of the femoral lateral cortex, the stub 2 advantageously has a slightly developed curved shape, for example curved by 6-8 degrees for the femur, 20-25 degrees for the tibia, 25-30 degrees for the humerus: the base of the stub 2 is conveniently slightly frustum-shaped and converges toward the couplings of the stems.

Means 10 for the temporary binding retention of the bundled stems are provided and for example comprise a metallic wire 11; a manual grip ring 12 is rigidly associated with said wire at one end and a bent portion 13, which is engaged on said wire and defines a loop 14, is rigidly associated with said wire at the other end; proximate to the ends, the stems 8 advantageously have respective grooves 15 in which the loop 14 can be accommodated while the wire runs between the curved stems 8 (see FIGS. 4 and 5); advantageously, the wire is passed through the axial hole 5 which is extended downward and conveniently has a lateral notch in the threaded region so as to indeed allow the passage of the wire.

In another provided and preferred embodiment (see FIG. 6) the temporary retention binding means 10 are obtained as follows: the ends 16 of the stems 8 are folded at 90 degrees toward the center, are traversed by small holes 17 and have appropriate lengths so that the holes align at the central axis of the stem bundle; the lower end of the metallic wire 11 is passed through the holes 17; in this embodiment, the upward traction of the wire 11, which allows the release of the stems, is extremely easy.

In another provided embodiment (FIG. 7), the temporary binding retention means 10 are constituted by an ogival cap 18 which is forced around the free ends of the bundled stems; the cap 18 is made of bio-absorbable material, and in order to release the tip of the stems the wire 11, of appropriate rigidity, is pushed downward; after a short time the cap is reabsorbed by the tissues.

FIG. 8 illustrates temporary binding retention means 10 constituted by a metallic wire 19 which is inserted in the grooves 15 of the stems, embraces the bundled stems and has its ends 20 mutually braided; the wire 19 is surmounted by a cable 21 which passes between two stems and is intended to be pulled so as to release the braided ends of the wire 20: the wire 20 remains coupled to one of the stems since it is passed through a hole of said stem or is tied onto the end thereof.

The temporary binding retention means 10 can also be constituted for example by bio-absorbable threads intended to be left in place after releasing the tips of the stems.

The operation of the pin according to the invention, for example for a femur prosthesis, is as follows:

a cylindrical channel F is provided in the proximal metaphysis A, extends downward through all of the metaphysis up to the medullary canal and is oriented along the axis of the bone: the pin according to the invention is inserted through said canal with the stems bundled, being aided in doing so by means of the handle 7 screwed to the proximal part of the stub: by using a radiographic examination means, the pin is caused to traverse the medullary canal until the end of the pin penetrates inside the medullary canal distally with respect to the fracture; the wire 11 is pulled, or pushed, by means of the manual grip ring 12 and releases the stems and allows them to open (for the embodiments shown in FIGS. 6 and 7, the wire 11 slips out of the holes 17 or pushes the cap 18 away); as the insertion of the pin continues, the stems 8, by divaricating, press the bone of the metaphysis B from the inside and anchor thereto.

The proximal stub can then be anchored to the cortices at A by means of a screw.

Attention is called to the fact that the fixing of the pin in the distal region of the fracture occurs without having to intervene from the outside on this region: torsional movements of the distal fragment are furthermore prevented, since the various stems arrange themselves on different planes.

The coupling which is furthermore provided between the two ends of the fracture, instead of being rigid, is slightly elastic, and this allows the more rapid forming of the bone callus which restores the continuity of the fractured bone.

When the fracture has consolidated, it is possible to extract the pin by first screwing the stem 6 of the handle 7 at 5 and by then simply pulling: the stems will slip out.

It should be noted that a small number of sizes of the invention are sufficient to be able to intervene on any type of patient and fracture and that no preliminary drilling or medullary canal preparation operations are required.

In the case of the femur, in order to adapt the pin to the natural procurvature of the bone in which it is inserted, the bundled stems are given a slight procurvature: this can be obtained either by providing right and left pins or by providing an appropriate curving device to be used shortly before the prosthesis is installed.

It has thus been observed that the invention achieves the proposed aim and objects.

The invention thus conceived is susceptible to numerous modifications and variations, all of which are within the scope of the inventive concept.

All the details may furthermore be replaced with other technically equivalent elements.

In practice, the materials employed, as well as the shapes and dimensions, may be any according to the requirements without thereby abandoning the scope of the protection of the following claims.

I claim:

1. Intramedullary pin with self-locking end for metadiaphyseal fractures of long bones, comprising a proximal stub, means for fixing said stub to proximal cortices, at least two curved and elastically deformable stems, ends defined by said deformable stems and being axially rigidly associated with said stub, free ends defined by said stems, said free ends having temporary binding retention means, said temporary binding retention means being adapted to keep said free ends of said stems mutually adjacent during insertion of the pin in a medullary canal through a metadiaphysis and to release said free ends when the pin is in correct position so as to allow elastic expansion of said stems, the free ends thereof anchored in the intramedullary spongy bone until they press against the inner walls of the bone, producing an integral coupling between the intramedullary pin and the bone, the pin further comprising a grip handle having a grip handle stem, and wherein a threaded axial hole for the screwing of said grip handle stem is provided on said stub, said handle being adapted to facilitate the operations of inserting and extracting the pin in the medullary canal.

2. Pin according to claim 1, wherein said temporary binding retention means comprise a metallic wire which has one folded end which couples to itself so as to define a loop which arranges itself at respective seats of the ends of the stems, said loop opening and releasing the stems upon traction of the wire.

3. Pin according to claim 2, wherein said stub is axially perforated for the passage of said metallic wire.

4. Pin according to claim 1, wherein said means for fixing the proximal stub comprise a threaded oblique hole in the stub, said pin further comprising a screw adapted to pass through the bone cortices, said screw having a stem, said stem being engageable with said threaded oblique hole.

5. Pin according to claim 1, wherein said stems have rounded ends and one of said stems is slightly longer.

6. Pin according to claim 1, wherein said temporary binding retention means comprise a metallic wire the end whereof is adapted to insert in related aligned holes which are provided in the corresponding ends of the stems which are folded at 90 degrees toward the axis of the stem.

7. Pin according to claim 1, wherein said temporary binding retention means comprise an ogival cap made of bio-absorbable material, said free ends of said stems being bundled together, said ogival cap being forced onto the bundled ends of the stems and pushed outward by a rigid metallic wire inserted along the bundle.

8. Pin according to claim 1, wherein said temporary binding retention means comprise a metallic wire the ends whereof are mutually braided, said ends being released by pulling a cable.

9. Pin according to claim 1, wherein said stems have a slight procurvature for improved binding of fractured femur bones.

10. An intramedullary pin (1) for metadiaphyseal fractures of long bones, comprising:
   a short proximal stub (2) for insertion and lodging in a first end of a bone;
   means (3) for rigidly fixing said short proximal stub in the first end of the bone;
   a plurality of curved and elastically deformable stems (8) connected to said short proximal stub and extending therefrom, said stems being sufficiently long so as to extend inside the bone from the first end thereof where said stub is inserted substantially to a second end thereof when the pin is fully inserted inside the bond, the stems having first ends which are connected to said short proximal stub and free ends (9) opposite to said first ends, the stems being curved such that said free ends are mutually spaced apart when said stems are in an undeformed state; and
   means (10) for temporarily retaining said free ends of said stems mutually bound together thereby to allow the pin to be inserted inside the bone, said means for retaining being releasable by a user after the pin is inserted inside the bone thereby to release said free ends of said stems which expand and press against the inner walls of the bone.

11. Pin according to claim 10, wherein said means for temporarily retaining said free ends of said stems mutually bound together comprise a metallic wire which has one folded end which couples to itself so as to define a loop which arranges itself at respective seats of the ends of the stems, said loop opening and releasing the stem upon traction of the wire.

12. Pin according to claim 11, wherein said stub is axially perforated for the passage of said metallic wire.

13. Pin according to claim 10, wherein said means for fixing the proximal stub comprise a threaded oblique hole in the stub, said pin further comprising a screw adapted to pass through the bone cortices, said screw having a stem, said stem being engageable with said threaded oblique hole.

14. Pin according to claim 10, wherein said stems have rounded ends and one of said stems is slightly longer.

15. Pin according to claim 10, wherein said means for temporarily retaining said free ends of said stems mutually bound together comprise a metallic wire the end whereof is adapted to insert in related aligned holes which are provided in the corresponding ends of the stems which are folded at 90 degrees toward the axis of the stem.

16. Pin according to claim 10, wherein said means for temporarily retaining said free ends of said stems mutually bound together comprise an ogival cap made of bio-absorbable material, said free ends of said stems being bundled together, said ogival cap being forced onto the bundled ends of the stems and pushed outward by a rigid metallic wire inserted along the bundle.

17. Pin according to claim 10, wherein said means for temporarily retaining said free ends of said stems mutually bound together comprise a metallic wire the ends whereof are mutually braided, said ends being released by pulling a cable.

* * * * *